United States Patent
Gerlach et al.

(10) Patent No.: US 12,042,622 B2
(45) Date of Patent: Jul. 23, 2024

(54) APPARATUS AND METHOD FOR OPENING AND CLOSING AN INFUSION TUBE CLAMP

(71) Applicant: B. BRAUN MELSUNGEN AG, Melsungen (DE)

(72) Inventors: Hans-Josef Gerlach, Marsberg (DE); Jürgen Steger, Körle (DE)

(73) Assignee: B. Braun Melsungen AG, Melsungen (DE)

( * ) Notice: Subject to any disclaimer, the term of this patent is extended or adjusted under 35 U.S.C. 154(b) by 1128 days.

(21) Appl. No.: 16/630,656

(22) PCT Filed: Jul. 18, 2018

(86) PCT No.: PCT/EP2018/069544
§ 371 (c)(1),
(2) Date: Jan. 13, 2020

(87) PCT Pub. No.: WO2019/016283
PCT Pub. Date: Jan. 24, 2019

(65) Prior Publication Data
US 2020/0164199 A1     May 28, 2020

(30) Foreign Application Priority Data
Jul. 18, 2017   (DE) ..................... 10 2017 116 106.6

(51) Int. Cl.
*A61M 39/28* (2006.01)
*A61M 5/142* (2006.01)
*A61M 5/168* (2006.01)

(52) U.S. Cl.
CPC ............ *A61M 39/28* (2013.01); *A61M 5/142* (2013.01); *A61M 5/16813* (2013.01); *A61M 39/281* (2013.01)

(58) Field of Classification Search
CPC .... A61M 39/28; A61M 39/281; A61M 5/142; A61M 5/16813
See application file for complete search history.

(56) References Cited

U.S. PATENT DOCUMENTS 3,960,149 A * 6/1976 Bujan ................. A61M 39/286
                                                        24/115 L
4,247,076 A * 1/1981 Larkin .................. A61M 39/28
                                                            251/9

(Continued)

FOREIGN PATENT DOCUMENTS

CN          1795937 A        7/2006
CN        101795724 A        8/2010

(Continued)

OTHER PUBLICATIONS

German Search Report for German Application No. 10 2017 116 106.6, with English translation, dated Feb. 28, 2018, 14 pages.

(Continued)

*Primary Examiner* — Nathan R Price
*Assistant Examiner* — Mark A Igel
(74) *Attorney, Agent, or Firm* — Christopher A. Rothe; Culhane PLLC (57) ABSTRACT

A device for opening and closing an infusion tube clamp includes a slide link which is axially arranged to be movable on a flap and includes at least one projecting locking element for closing an infusion tube clamp. An infusion tube clamp includes a first clamping leg and a second clamping leg pivotally connected to each other at one end, and a keeper plate which is arranged on the first clamping leg. At the locking element, the slide link includes a slide link ramp at which a switching cam of the keeper plate is adapted to slide into a stress-free final closing position.

6 Claims, 5 Drawing Sheets

(56) References Cited

U.S. PATENT DOCUMENTS

| | | | | |
|---|---|---|---|---|
| 5,219,327 | A * | 6/1993 | Okada | A61M 39/281 |
| | | | | 417/474 |
| 5,630,710 | A * | 5/1997 | Tune | A61M 5/172 |
| | | | | 417/326 |
| 5,904,668 | A | 5/1999 | Hyman et al. | |
| 6,261,262 | B1 | 7/2001 | Briggs et al. | |
| 6,629,955 | B2 * | 10/2003 | Morris | A61M 5/14228 |
| | | | | 604/153 |
| 8,328,763 | B2 * | 12/2012 | Traversaz | A61M 5/14244 |
| | | | | 604/250 |
| 8,430,654 | B2 * | 4/2013 | Kasai | F04B 43/12 |
| | | | | 417/474 |
| 9,028,456 | B2 * | 5/2015 | Kasai | A61M 39/281 |
| | | | | 604/249 |
| 2001/0049507 | A1 * | 12/2001 | Ishida | A61M 5/3273 |
| | | | | 251/9 |
| 2007/0270765 | A1 * | 11/2007 | Hasler | A61M 5/14228 |
| | | | | 604/246 |
| 2008/0091150 | A1 * | 4/2008 | Murphy | A61M 5/16809 |
| | | | | 604/250 |
| 2009/0254034 | A1 * | 10/2009 | Beck | A61M 39/283 |
| | | | | 604/246 |
| 2009/0306592 | A1 * | 12/2009 | Kasai | F04B 49/10 |
| | | | | 604/131 |
| 2010/0036322 | A1 * | 2/2010 | Rotem | A61M 5/14228 |
| | | | | 604/151 |
| 2010/0040481 | A1 * | 2/2010 | Wolff | A61M 39/281 |
| | | | | 417/437 |
| 2012/0004624 | A1 * | 1/2012 | Brown | A61M 39/287 |
| | | | | 604/250 |
| 2012/0035581 | A1 * | 2/2012 | Travis | A61M 39/287 |
| | | | | 604/249 |
| 2013/0138074 | A1 * | 5/2013 | Travis | A61M 39/287 |
| | | | | 604/151 |
| 2014/0074047 | A1 * | 3/2014 | Calderon | A61M 39/28 |
| | | | | 604/250 |
| 2014/0336613 | A1 * | 11/2014 | Roth | A61M 39/28 |
| | | | | 604/500 |

FOREIGN PATENT DOCUMENTS

| | | |
|---|---|---|
| CN | 101990447 A | 3/2011 |
| CN | 102971029 A | 3/2013 |
| CN | 104324432 A | 2/2015 |
| DE | 8508371 U1 | 5/1985 |
| DE | 69826474 T2 | 2/2005 |
| EP | 0813430 B1 | 8/1999 |
| EP | 2583716 A1 | 4/2013 |
| JP | H4166167 A | 6/1992 |
| JP | 2004073822 A | 3/2004 |
| JP | 2011212112 A | 10/2011 |
| WO | 8704932 A1 | 8/1987 |
| WO | 2011121923 A1 | 10/2011 |

OTHER PUBLICATIONS

International Search Report and Written Opinion for International Application PCT/EP2018/069544, dated Nov. 19, 2018, 11 pages.
Office Action received in Chinese Application No. 201880047943.6 dated Sep. 3, 2021, with translation, 12 bages.

* cited by examiner

APPARATUS AND METHOD FOR OPENING AND CLOSING AN INFUSION TUBE CLAMP

CROSS-REFERENCE TO RELATED APPLICATIONS

This application is the United States national phase entry of International Application No. PCT/EP2018/069544, filed Jul. 18, 2018, which claims the benefit of priority of German Application No. 10 2017 116 106.6, filed Jul. 18, 2017. The contents of International Application No. PCT/EP2018/069544 and German Application No. 10 2017 116 106.6 are incorporated by reference herein in their entireties.

FIELD

The invention relates to a device and a method for opening and closing an infusion tube clamp, wherein upon closing and opening of a flap the infusion tube clamp is closed and can be opened in the final closing position of the flap; the device comprising a slide link including a locking element which has a slide link ramp and including a keeper plate which has a switching cam and is connected to a pivoting clamping leg of an infusion tube clamp.

BACKGROUND

In medical engineering, infusion tube pumps are known in which the medium to be delivered is pressed by external mechanical deformation of the tube by means of a rotor head through said tube (squeeze pump principle). In pumps of this type safety or tube clamps are employed at the tube as a standard so as to prevent so-called "free flow", abbreviated to FFC (free flow clamp). By the term "free flow" the gravitation flow is understood which may possibly result in dangerous over-infusion. As a standard, the clamps are located directly on the infusion tube so as to suppress or enable flow of infusion fluid through the infusion tube. For inserting an infusion tube into an infusion pump usually a pump flap hinged to a pump casing is opened and, in the case of stationary safety clamps in the infusion pump, the tube is inserted into the same.

Generally, safety clamps are usually opened or closed indirectly by force by manual operation of the pump flap of the infusion pump so as to suppress quasi automatically undesired flow of the fluid through the infusion tube. It may occur in this context that the safety clamp has to be directly closed manually before the pump flap can be regularly closed. However, frequently at first the tube-side safety clamp is directly closed manually and then is indirectly opened (automatically) again upon closing of the pump flap. A tube clamp being closed after closing the pump flap can be directly opened automatically again for pump operation by means of an actuator of the infusion pump. Apart from infusion pumps having such opening function, there are existing actuators for a corresponding closing function for closing the tube-side safety clamp.

EP 0 813 430 B1 discloses a flow stop mechanism which automatically closes a flexible tube when no cassette is provided in a pump. If no cassette is provided in the pump, the tube can be opened by manually actuating a pin.

EP 2 583 716 A1 discloses an infusion tube clamp and a method of making use of the infusion tube clamp. The tube clamp comprises a base structure including an infusion pump receiving area as well as a first clamping leg and a second clamping leg for squeezing the received infusion tube. The clamping legs are pivotally connected to each other at one end. The infusion tube clamp includes a snap-fit for safely positioning the two clamping legs at more than one position.

When, according to the known state of the art, the tube or safety clamp is a single-use article, incomplete closing (or opening) of the tube clamp and consequently "free flow" may possibly occur—due to tolerances in manufacture of the tube clamp—especially in the case of an indirect actuating design e.g. via actuation of the pump casing flap. Furthermore, single-use safety clamps have to be inserted in the pump casing with tolerances so that the mostly mechanical interaction between the clamping mechanism and the actuating mechanism of the flap hinged to the pump casing, for example, does not perfectly work.

SUMMARY

Therefore, it is the object of the invention to provide a device for opening and/or closing an infusion tube clamp which enables safe opening and closing and has small tolerances in manufacture and/or is not susceptible to tolerances on the side of the tube/safety clamp (designed as a single-use article). Another objective of the invention resides in the easy handling and in the reduction of the possibility of human failure.

The basic concept of the present invention thus provides a closing device (closing mechanism) for a flap hinged to a pump casing which simultaneously effectuates also (indirect) actuation (closing and opening) of at least one safety/tube clamp (preferably of the single-use type) fixed/fixable within the pump casing. According to the invention, in the actuating/clamping force train between the closing mechanism and the safety clamp an elastic component having a defined spring rigidity is arranged which compensates tolerances in the actuating force train for example due to manufacturing and/or mounting tolerances especially on the side of the safety clamp. The spring rigidity is chosen so that, upon actuating the closing device, a clamping force is applied to the tube/safety clamp which at most results in complete squeezing of a tube inserted therein.

Basically, in conformity with the state of the art, the safety clamp employed in the invention includes two clamping elements or clamping jaws preferably pivotally movable relative to each other which in the (closed) clamping position engage in each other via a snap lug formed/arranged on a spring tongue. For opening the safety clamp, equally in conformity with the state of the art, an actuator (e.g. a piston-cylinder arrangement) is provided for pressing against the snap lug and moving the latter out of the engaged position.

The closing mechanism according to the invention now includes a slide or locking bar supported or adapted to be supported on the flap and including a link forming at least one open slit which link undercuts at least one pin or bolt (bolt lock) disposed/formed on the pump casing when the locking bar is axially displaced in the direction of the closing position, and thus increasingly pulls the flap against the pump casing when the locking bar is axially displaced in the direction of the closing position.

Further, at the locking bar an actuating element, preferably a pressing plate/keeper plate having an inherent elasticity or an internal spring mechanism is mounted, preferably hinged pivotally and relatively axially movably, which actuating element, when the locking bar is axially displaced in the direction of the closing position (via a switching cam formed thereon) against a ramp-shaped stop (locking element including slide link ramp formed thereon), rests on the locking bar and in this way, upon axial displacement of the locking bar relative to the actuating element, exerts an (increasingly resilient) pressing force on at least one clamping jaw of the safety clamp so as to move the latter in the direction of the clamping position, until the snap lug is engaged.

Upon reaching the maximum closing position of the locking bar at the latest, the locking bar-side stop completely overruns the actuating element and thus releases the actuating element, preferably the pressing plate. The safety clamp now can be easily opened by means of the actuator, while the flap is completely closed and locked, so as to release a fluid flow.

For opening the flap, the locking bar is withdrawn from the closing position, with the locking bar-side stop again abutting against the actuating element, thus causing the one clamping jaw of the safety clamp to be (resiliently) forced into the clamping position in which the snap lug is again engaged. The flap now can be completely unlocked and opened without the engaged safety clamp opening.

In other words, the device for opening and closing an (infusion) tube clamp in a preferred embodiment includes a slide link (locking bar) that is axially arranged/adapted to be arranged to be movable on a flap of a pump casing and has at least one handle for closing the tube clamp. Moreover, the device includes the (infusion) tube clamp having a first clamping leg (clamping jaw) and a second clamping leg (clamping jaw) which are pivotally connected to each other at one end, and an actuating element/keeper plate arranged on the first clamping leg. The slide link further includes a slide link ramp (stop) with a switch cam of the keeper plate sliding off the latter, when the slide link is axially displaced relative to the keeper plate, and finally being adapted to slide into a tension-free final closing position.

In a preferred embodiment, the slide link/slide/locking bar is provided to be axially movable via a lever joint/knee lever which in turn is connected to a handle/grip handle. The movement of rotation of the handle is thus converted to an axial movement of the slide link. The slide link is axially movable at its longitudinal axis, with the slide link preferably resting on an upper edge of the flap/door or the like and the axial direction thus being parallel to the flap front/flap cover front.

In another embodiment, in a closed state the infusion clamp has different positions, especially a stress-applying position and a stress-free position. The actuating element/keeper plate is in pressurizing mesh in the stress-applying position by the locking element/stop and is in pressure-less mesh with the locking element/stop in the stress-free position. In other words, the flap is closed and the locking element/stop can be pressed against/is in mesh with the keeper plate/actuating element, therefore the latter is in a stress-applying position, wherein the stress-free state can also be understood to be a lower-stress state or a contact without pressure. The stress-free position is reached in the closing end position.

In another embodiment, when the flap is closed, the infusion tube clamp is closing in the stress-applying position and can be opened in the stress-free position. In other words, the infusion tube clamp can be closed by the slide link and thus, in a stress-applying position and by the movability of the slide link to the final closing position at which the slide link is disengaged from the keeper plate, is openable and thus can be opened, hence is in a stress-free position.

In another embodiment, the locking element/stop is formed at the slide link in the form of an angular member, preferably at an angle of substantially 90°. In other words, the slide link is flat and approximately strip-shaped (sheet metal component). The cross-section in the area of the locking element which is not continuous in the longitudinal direction of the slide link takes an angular shape. The locking element/stop thus is configured in L shape integrally with the slide link. The stop may be vertical, hence at right angles, but it may as well take any other shape or any other angle for actuating the keeper plate.

In another embodiment, the keeper plate is a, preferably one-part, spring steel sheet (leaf spring). In other words, the keeper plate may have an inherent resilience. It is also possible, however, to form the keeper plate of two elements/plates that are connected to be movable relative to each other (e.g. via a hinge), wherein a separate spring element is disposed between the two elements/plates so that an internal resilience is imparted to the keeper plate.

In another embodiment, the device includes an electrically or manually operable actuator. When the infusion tube clamp is in a closed state and the latch/snap lug at the clamp locks the same, the actuator present in the pump casing is provided and adapted to operate said snap lug and to open the infusion tube clamp, with the opening of the infusion tube clamp/the swinging open of the clamping legs is possible only when the keeper plate is in the final closing position in an axial area of the slide link that includes no locking element/stop.

In another embodiment, the slide link ramp is in constant sliding contact with the switching cam. In other words, the switching cam has a slanted machined area that is in contact with the locking element/stop even in the final closing position. In said position the switching cam of the keeper plate still contacts the slide link ramp of the locking element/stop of the slide link, but it is no longer pressurized by the same, however. Said contact merely serves for enabling the switching cam to slide into/onto the locking element/stop again when opening the flap and, resp., unlocking the flap. As an alternative to this, the infusion tube clamp may also include a flap angle limiter which prevents the first flap leg from completely unfolding; therefore, here no contact is required any more between the slide link and the keeper plate.

In a preferred embodiment, a method of opening and closing an infusion tube clamp is illustrated in which, upon closing and opening a flap of the pump casing, the infusion tube clamp is closed and can be opened at the final closing position of the flap. The flap is closed and a locking element/stop of an axially movable slide link is pressed against a switching cam of a (resilient) keeper plate/actuating element, thus causing an infusion tube clamp to be closed. The switching cam slides off a slide link ramp for reaching the final closing position, whereupon no more force is applied to the keeper plate. An actuator can open the infusion tube clamp in the final closing position of the slide link. When the flap is opened, the infusion tube clamp is closed (automatically/by force) by inverse axial displacement of the slide link.

In other words, the flap is closed, with the slide link pressing against the keeper plate and thus also closing the infusion tube clamp, while the slide link is moving in the direction of the final closing position. Accordingly, the locking element of the slide link presses against the switching cam of the keeper plate disposed at/adjacent to the first clamping leg of the infusion clamp. The first clamping leg together with the keeper plate thus folds against the second clamping leg and closes the clamp and, resp., closes an opening in an infusion tube by squeezing. The slide link continues moving in an axial direction and thus the switching cam slides off the slide link ramp and the keeper plate is relieved. Since the keeper plate now does no longer compress the infusion tube clamp, the latter now can be opened by the actuator. By opening it is meant that the infusion tube is no longer completely squeezed between the clamping legs and has a through-opening for infusion fluid. The switching cam of the keeper plate slides off the slide link ramp at the slide link before the final closing position of the slide link is reached, wherein this is realized by the beveled area of the ramp and of the switching cam. In the final closing position of the slide link, the switching cam may still be in (loose) contact with the ramp but may as well be free-standing.

In a preferred embodiment, the slide link reaches the final closing position by being displaced in an axial direction. The slide link is supported to be axially movable on/at an edge area of the flap.

BRIEF DESCRIPTION OF THE DRAWING FIGURES

The invention will be illustrated in detail with reference to the drawings in which one embodiment is exemplified.

DETAILED DESCRIPTION

Figure 1:
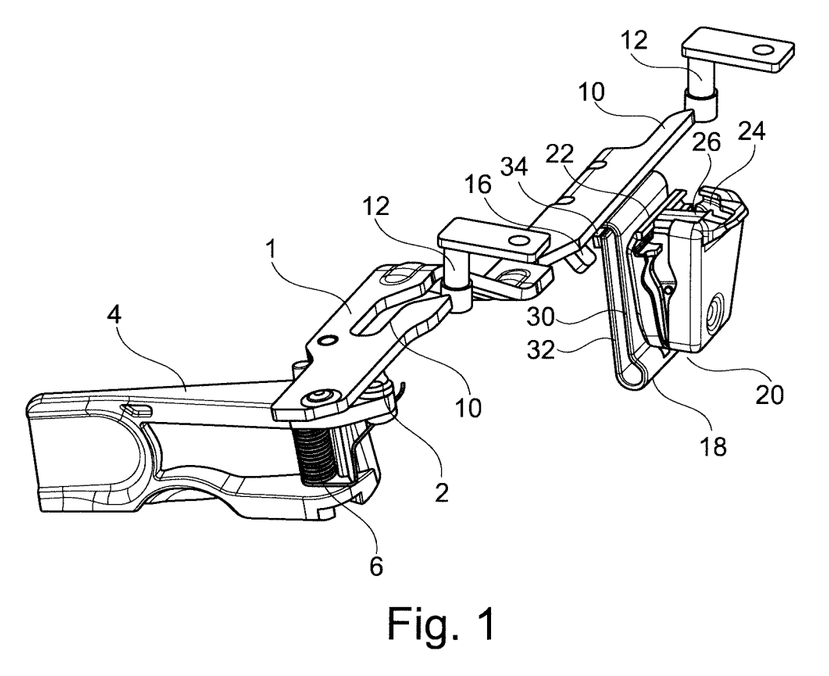
FIG. 1 shows a perspective view of the components of the device devoid of the casing.

FIG. 1 illustrates a perspective view of the components of a device according to the invention and, resp., a mechanism according to the invention for opening and closing an (infusion) tube clamp devoid of a complete casing of an (infusion) pump not shown in detail, preferably of the squeeze pump type. Accordingly, the device comprises a slide link or slide/locking bar 1 supported or adapted to be supported on a flap (cf. FIG. 4) of an infusion pump casing (cf. FIG. 4) that is connected to a handle/flap handle 4 via a lever joint 2. The handle 4 is pivotally coupled or adapted to be coupled to the flap of the infusion pump casing not shown in detail in the area of the lever joint 2 and is biased by means of a spring/handle spring 6 in a first pivoting direction (closing direction). A rotating/pivoting movement of the handle 4 is thus converted by the lever joint 2 into an axial movement of the slide link 1 along the flap. The slide link 1 may thus be displaced along its longitudinal axis 8 by pivoting the handle 4 at a transmission ratio determined corresponding to the design of the knee lever joint 2. By displacing the slide link 1 guide grooves 10 formed in the slide link 1 are engaged with pins/bolts preferably including rolls 12 that are arranged at the casing/infusion pump casing of the infusion pump casing. Due to said engagement, the slide link 1 and thus the flap (not shown in detail) on which the slide link 1 is supported can be pulled to the casing (equally not shown in detail). The slide link 1 includes an area at which a stop/locking element 16 is formed. The locking element 16 protrudes downwards, i.e. against the flap edge and preferably is configured at the slide link 1 in the form of a curved projection. In the area in which the (at least one) locking element 16 is configured, on the corresponding side of the infusion pump casing, i.e. directly opposed when the flap 14 is closed, an actuating element/ keeper plate 18 which is adjacent to an infusion tube clamp 20 is disposed. The slide link 1 thus moves in its axial longitudinal direction, while the infusion tube clamp 20 and the pins 12 are arranged to be fixed/stationary on the casing. The keeper plate 18 is preferably hinged to the slide link 1, as shown in FIG. 1, such that the slide link 1 is axially movable relative to the keeper plate 18. Alternatively, the keeper plate 18 may as well be articulated/mounted to the pump casing or to the flap.

The infusion tube clamp 20 includes a first clamping leg 22 and a second clamping leg 24. The second leg 24 is disposed at the casing of the infusion pump and is connected to the first clamping leg 22 in a foldable/pivoted manner at a lower end. Since the keeper plate 18 is merely adjacent to the first clamping leg 22, also the keeper plate 18 is pivoted relative to the second clamping leg 24 and thus relative to the casing of the infusion pump. Moreover, the infusion tube clamp 20 includes a snap fit or lug 26 at its upper end so that the first clamping leg 22 can engage in the second clamping leg 24 in a clamp closing position.

Figure 2:
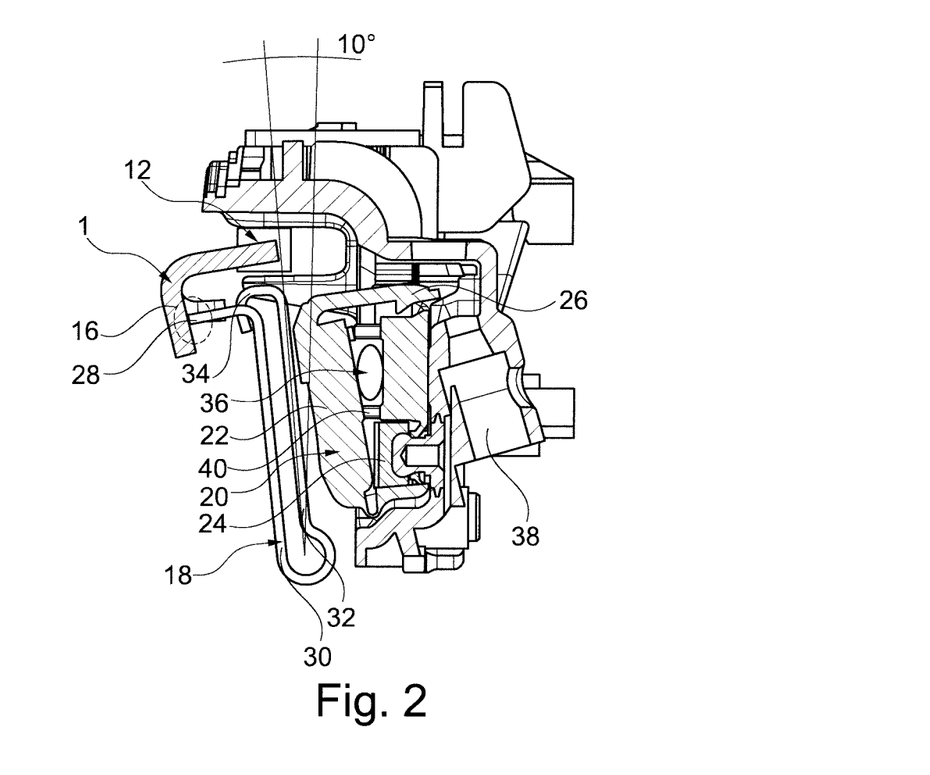
FIG. 2 shows a sectional view across the device within the casing in a first closing position (open flap position)

FIG. 2 illustrates a sectional view across the device in the casing in a first closing position (open flap position), more exactly speaking in a position in which the first clamping leg 22 has an angle of preferably 10° relative to the second clamping leg. This means that the flap is substantially closed, but the handle 4 has not yet been actuated. In this view, a switching cam 28 is visible which extends from the keeper plate 18 in the direction of the closed flap and is in contact with the stop/locking element 16. The keeper plate 18 incidentally includes a first keeper spring plate leg 30 and a second keeper spring plate leg 32 which are connected preferably adhesively to each other in U or V shape. The second keeper plate leg 32 is fastened to the first clamping leg 22 and is connected at a lower end to the first keeper plate leg 30 such that it is pivoting according to the spring principle. At the first keeper plate leg 30 the switching cam 28 is integrally arranged to project at a predetermined angle, preferably 90°. At the second keeper plate leg 32 a wraparound or eyelet 34 is formed which is preferably semicircular and engages in the first keeper plate leg 30 so as to delimit said opening angle. This means that the wrap-around 34 of the second keeper plate leg 32 engages with the first keeper plate leg 30 and keeps the same tensioned and prevents the keeper plate 18 from unfolding. Moreover, the wrap-around 34 may be in the form of a hinge for pivotal coupling to the slide link 1.

In the first closing position, it is further evident in which way the infusion tube 36 is located between the clamping legs 22 and 24 in an open/non-squeezed state. Furthermore, in this view also an actuator 38 for opening the snap lug 26 is visible. The actuator 38 may press from the bottom to the end of the snap lug 26 projecting from the infusion tube clamp 20 and in this way disengage the same as well as thus also open the infusion tube clamp 20, as will be illustrated in a later step. Between the two clamping legs 22 and 24 a clamping leg opening angle limiter 40 that is adapted to limit the relative opening angle is shown. In this context, it is outlined once again that the term "bottom" in the representation of FIG. 2 refers to direction pointing to the lower sheet end and hence to the direction in which the pivoting ends of the clamp 20 are located.

Figure 3:
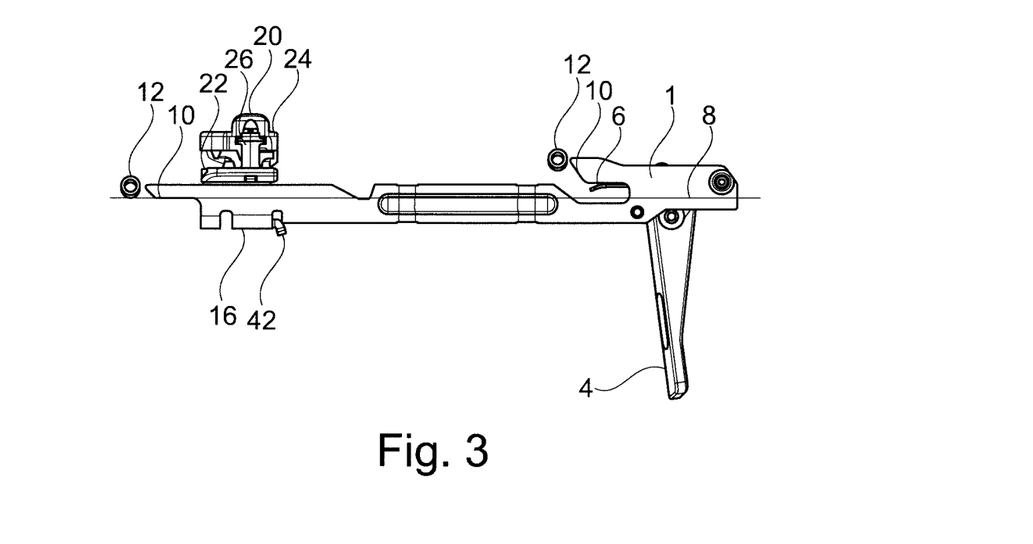
FIG. 3 shows a top view onto the components in a first closing position (open flap position)

FIG. 3 illustrates a top view onto the components in a first closing position (open flap position). In this view, the slide link 1 is shown in a non-actuated state while the flap 14K is substantially closed. The slide link 1 is not in contact with the pins 14 but already presses to the switching cams 28 of the keeper plate 18. The handle 4 is in a completely opened position extending to about 85° to 90° relative to a longitudinal axis 8 of the slide link 1, with the longitudinal axis 8 extending along the flap and, resp., the slide link 1. Clearly evident from this representation is the curved locking element (stop) 16 on the side of the slide link 1 in an area opposed to the infusion tube clamp 20 at the casing of the infusion pump 14g. The locking element 16 is in the form of a downwardly bent angle and thus projects from the bar-shaped slide link 1 like a tooth. On the side of the locking element 16 facing the keeper plate 18, a slide link ramp 40 is formed. Said slide link ramp 40 extends in the longitudinal direction of the longitudinal axis toward the handle 4 and at one longitudinal end is outwardly curved/beveled/bent in the direction of the flap front.

Figure 4:
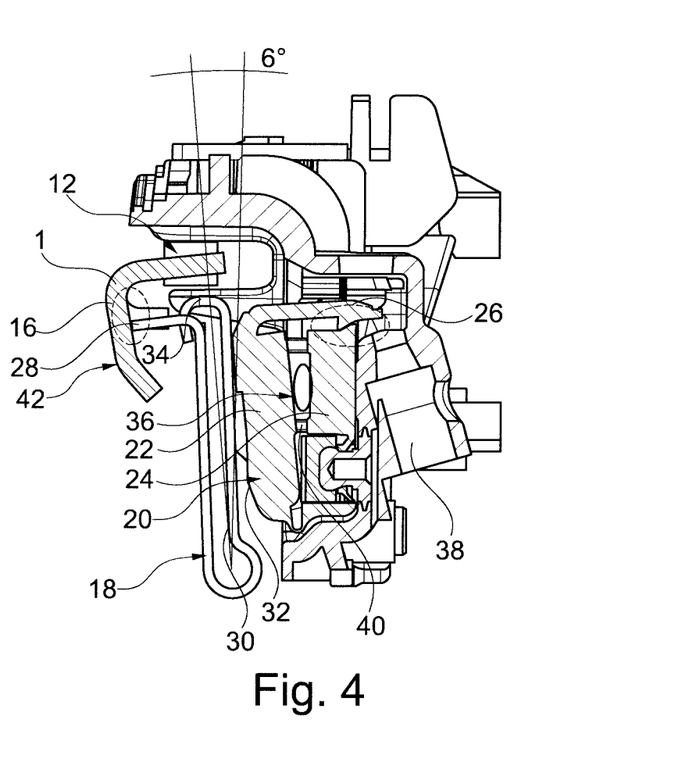
FIG. 4 shows a sectional view across the device within the casing in a second closing position (semi-opened flap position)

FIG. 4 illustrates a sectional view across the device in a second closing position (semi-open flap position). In this position the force transmission through the flap handle 4 has started. This means that the flap handle 4 adopts an angle relative to the slide link 1 that is smaller than its completely open position, preferably smaller than 85°, relative to the longitudinal axis of the slide link 1. The slide link 1 moves along the longitudinal axis 8 and engages in the pins 12. The pins 12 thus are provided within the catch range of the slide link 1, especially of the longitudinal slits 10 formed on the same. By engagement of the slide link 1 with the pins 12, the slide link 1 and thus the flap 14k moves in the direction of the infusion pump casing 14g, i.e. in the closing direction of the flap 14k. By the movement of the flap 14k in the direction of the infusion pump casing 14g the slide link 1 presses the switching cam 28 and thus the keeper plate 18 with the first clamping leg 22 against the second clamping leg 24. The two legs 22 and 24 pivot/fold toward each other and start squeezing the infusion tube 36.

The opening angle of the two clamping legs shown in FIG. 4 in this position amounts to about 6°. The snap lug 26 is not yet closed/engaged.

Figure 5:
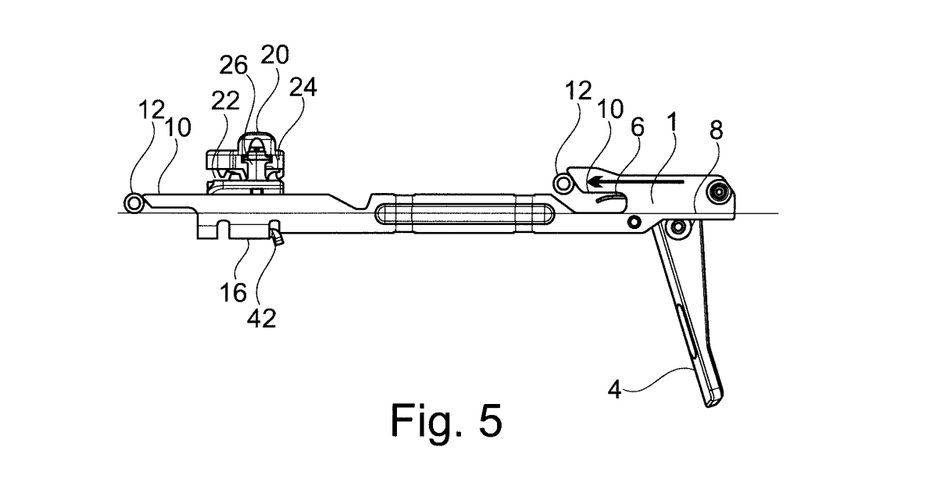
FIG. 5 shows a top view onto the components in a second closing position (semi-opened flap position)

FIG. 5 illustrates a top view onto the components in a second closing position (semi-open flap position). From this view it is clearly evident that the handle 4 is no longer in its completely opened position and the pins 12 are provided within the catch range of the guiding grooves/slits 10. Moreover, the slide link 1 has continued moving in the arrow direction along the longitudinal axis of the slide link 1 as compared to FIG. 3.

Figure 6:
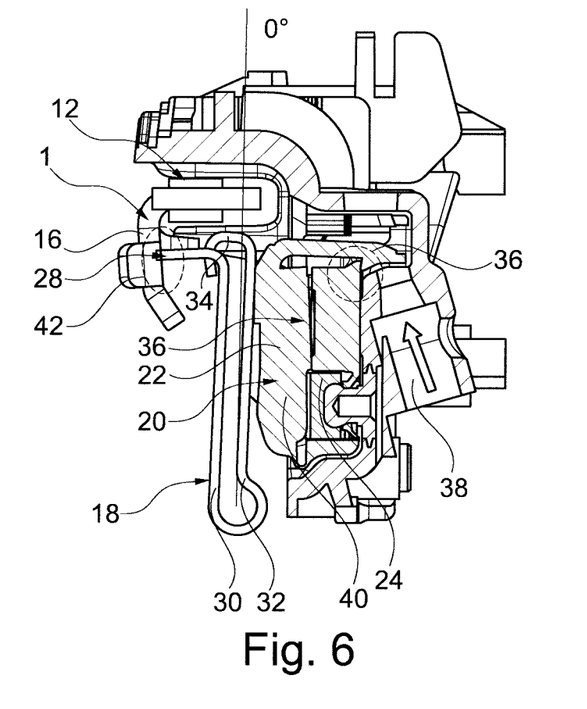
FIG. 6 shows a sectional view across the device within the casing in a third closing position (closed flap position)

FIG. 6 illustrates a sectional view across the device in a third closing position (closed flap position). The infusion tube clamp 20 is completely closed in this position. This means that the infusion tube 36 is completely squeezed by the two clamping legs 22 and 24 so that no infusion fluid can pass through the infusion tube. The keeper plate 18 is pressurized by the locking element 16. The snap lug 26 is provided in an engaged position. In this representation, the lateral view of the slide link ramp 42 at which the switching cam 28 starts sliding off the ramp 42 is evident. The flap 14k and thus the slide link 1 now are provided in a completely closed position relative to the infusion pump casing 14g.

Figure 7:
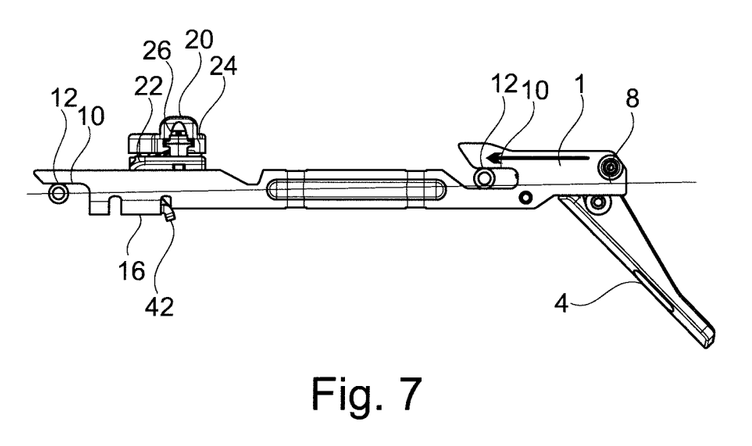
FIG. 7 shows a top view onto the components in a third closing position (closed flap position)

FIG. 7 illustrates a top view onto the components in a third closing position (closed flap position). The pins 12 slide into a slotted hole area of the respective guiding grooves/slits 10, the respective slotted hole area being oriented in parallel to the longitudinal axis 8 of the slide link 1. In this position, the switching cam 28 starts—due to the geometry thereof—sliding off the slide link ramp 42. The geometry of the switching cam 28 comprises a surface which is oriented in parallel to the longitudinal axis 8, namely in a front area located in the direction of the handle 4, and then includes a beveling at its rear area.

Figure 8:
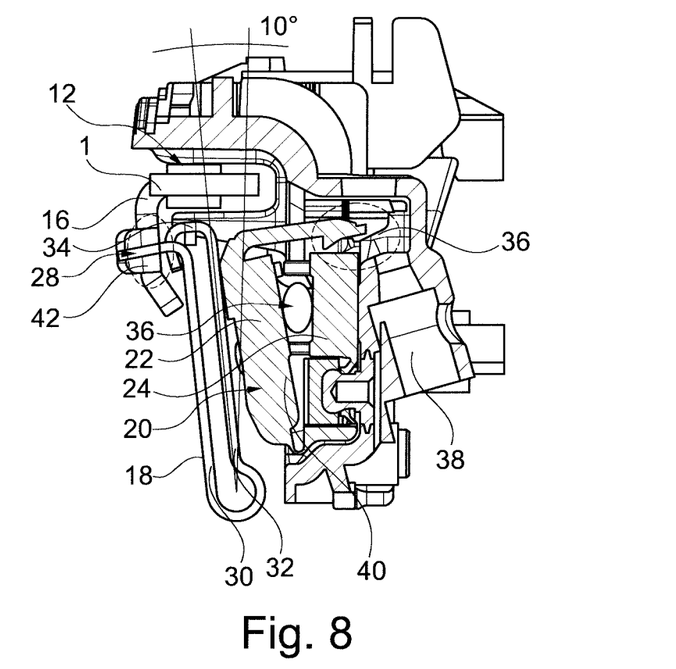
FIG. 8 shows a sectional view across the device within the casing in a fourth closing position (final flap position)

FIG. 8 shows a sectional view across the device in a fourth closing position (flap end position), i.e. when the handle 4, the flap 14k and the slide link 1 are provided in a final closing position. The slide link 1 is displaced/shifted so far in the arrow direction/closing direction of the longitudinal axis 8 that the switching cam 28 has slid off the slide link ramp 42 so far that, when the snap lug 26 is opened by the actuator 38, the keeper plate 18 is no longer supported on the ramp and thus the first clamping leg 22 may unfold. The keeper plate 18 becomes so-to-speak low-stress/stress-relieved/stress-free and does no longer compress the two clamping legs 22 and 24. By opening the infusion tube clamp 20 the infusion tube is no more or minimally squeezed/clamped and thus infusion fluid can flow therethrough again.

Figure 9:
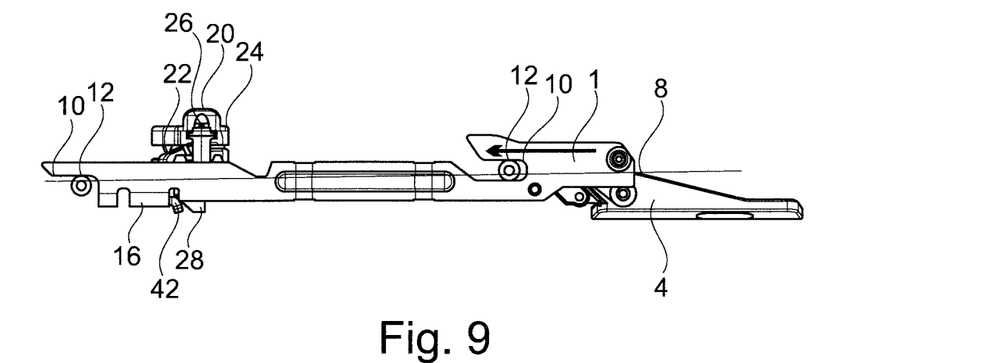
FIG. 9 shows a top view onto the components in a fourth closing position (final flap position).

FIG. 9 shows a top view onto the components in the fourth closing position (final flap position). In this case, it is especially evident that in the final closing position the handle 4 is in parallel to the slide link, the switching cam 28 has slid off the slide link ramp 42 and the keeper plate 18 thus is not pressed to abut against the one clamping leg.

For opening the flap 14k, the flap handle 4 is actuated. In this way, the slide link 1 is pulled against the arrow direction in FIG. 9. Thus, the switching cam 28 slides along the slide link ramp 42. Hence the infusion tube clamp 20 is closed again by force upon opening (opening operation) of the flap 14k and the flap 14k can be completely opened. Thus, the infusion tube clamp 20 is always automatically closed upon opening and closing of the flap 14.

The invention claimed is:

1. A closing mechanism of a tube clamp comprising a slide link which is configured to be movably arranged axially on a flap pivoted on a casing so as to pull the flap against the casing and to lock the same, by axially moving the slide link relative to the flap, wherein the tube clamp fixed in the casing has a first clamping leg and a second clamping leg, which are pivotably connected to each other at one end, wherein the slide link includes at least one locking element provided for closing the tube clamp while the slide link is axially moved, wherein an actuating element arranged on the first clamping leg is arranged between the slide link and the tube clamp for transmitting a clamping force from the locking element to the tube clamp as the at least one locking element is axially moved relative to the actuating element in a direction of a closing position, the actuating element having resilience of a defined spring rigidity, wherein the at least one locking element releases the actuating element to release the clamping force from the locking element to the tube clamp so long as the at least one locking element is in the closing position.

2. The closing mechanism according to claim 1, wherein the closing mechanism is configured so that, when the flap is already closed, the slide link adopts a stress-applying or pressurizing position at which the actuating element is in pressurizing engagement with the tube clamp by the at least one locking element of the slide link and adopts a stress-free or pressure-free position which constitutes the position locking the flap and at which the actuating element is in pressure-less contact with the tube clamp so as to enable opening of the tube clamp while the flap is closed.

3. The closing mechanism according to claim 2, wherein a slide link ramp is formed at the at least one locking element of the slide link to which a switching cam of the actuating element is slidingly adjacent such that, when the slide link is longitudinally displaced from the tensioning stress-applying or pressurizing position in the direction of the stress-free or pressure-free position, the clamping force is continuously increasing and, upon reaching the stress-free or pressure-free position, slides off the slide link ramp.

4. The closing mechanism according to claim 1, wherein the at least one locking element is configured at the slide link in the form of an angular element.

5. The closing mechanism according to claim 1, wherein the actuating element is V or U-shaped in cross-section.

6. A closing mechanism of a tube clamp comprising a slide link which is configured to be movably arranged axially on a flap pivoted on a casing so as to pull the flap against the casing and to lock the same, by axially moving the slide link relative to the flap,
- wherein the tube clamp fixed in the casing has a first clamping leg and a second clamping leg, which are pivotably connected to each other at one end,
- wherein the slide link includes at least one locking element provided for closing the tube clamp while the slide link is axially moved,
- wherein an actuating element arranged on the first clamping leg is arranged between the slide link and the tube clamp for transmitting a clamping force from the locking element to the tube clamp as the at least one locking element is axially moved relative to the actuating element in a direction of a closing position, the actuating element having resilience of a defined spring rigidity,
- wherein the at least one locking element releases the actuating element upon reaching the closing position,
- wherein the closing mechanism is configured so that, when the flap is already closed, the slide link adopts a stress-applying or pressurizing position at which the actuating element is in pressurizing engagement with the tube clamp by the at least one locking element of the slide link and adopts a stress-free or pressure-free position which constitutes the position locking the flap and at which the actuating element is in pressure-less contact with the tube clamp so as to enable opening of the tube clamp while the flap is closed, and
- wherein a slide link ramp is formed at the at least one locking element of the slide link to which a switching cam of the actuating element is slidingly adjacent such that, when the slide link is longitudinally displaced from the tensioning stress-applying or pressurizing position in the direction of the stress-free or pressure-free position, the clamping force is continuously increasing and, upon reaching the stress-free or pressure-free position, slides off the slide link ramp.

* * * * *